(12) United States Patent  
Dubois et al.

(10) Patent No.: US 9,766,170 B2  
(45) Date of Patent: Sep. 19, 2017

(54) DETERMINATION OF YOUNG'S MODULUS OF POROUS THIN FILMS USING ULTRA-LOW LOAD NANO-INDENTATION

(71) Applicant: INTERNATIONAL BUSINESS MACHINES CORPORATION, Armonk, NY (US)

(72) Inventors: Geraud J. Dubois, Los Altos, CA (US); Jane E. Frommer, San Jose, CA (US); Robin S. King, Half Moon Bay, CA (US); Krystelle Lionti, Campbell, CA (US); Kumar R. Virwani, San Jose, CA (US); Willi Volksen, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 262 days.

(21) Appl. No.: 14/607,291

(22) Filed: Jan. 28, 2015

(65) Prior Publication Data

US 2016/0216184 A1    Jul. 28, 2016

(51) Int. Cl.
*G01N 3/42*    (2006.01)

(52) U.S. Cl.
CPC ....... *G01N 3/42* (2013.01); *G01N 2203/0218* (2013.01); *G01N 2203/0286* (2013.01)

(58) Field of Classification Search
CPC ............. G01N 3/42; G01N 2203/0218; G01N 2203/0286; G01N 3/44; G01N 2203/0208
USPC ...................................................... 73/78–85
See application file for complete search history.

(56) References Cited

U.S. PATENT DOCUMENTS

| | | | |
|---|---|---|---|
| 3,490,273 A | | 1/1970 | Warfield et al. |
| 4,794,798 A | | 1/1989 | Matsushita et al. |
| 5,847,283 A | | 12/1998 | Finot et al. |
| 6,134,954 A | * | 10/2000 | Suresh .................. G01N 3/42 702/156 |
| 6,311,135 B1 | | 10/2001 | Suresh et al. |
| 6,494,840 B1 | * | 12/2002 | Mak ..................... A61B 8/485 600/443 |

(Continued)

OTHER PUBLICATIONS

Mogilnikov, et al.; Determination of Young's Modulus of Porous Low-k Films by Ellipsometric Porosimetry; Electrochemical and Solid-State Letters, 5 (12); Oct. 9, 2002; pp. F29-F31.

Winer, et al.; Mechanical Engineering Series, Nanoindentation Third Edition; Springer Science Business Media 2011; 17 pages.

Oliver, et al.; Measurement of hardness and elastic modulus by instrumented indentation: Advances in understanding and refinements to methodology; J. Mater. Res., vol. 19, No. 1, Jan. 2004; 18 pages.

(Continued)

*Primary Examiner* — Hezron E Williams
*Assistant Examiner* — Marrit Eyassu
(74) *Attorney, Agent, or Firm* — Schmeiser, Olsen & Watts (57) ABSTRACT

A method and computer product program for determining Young's modulus. The method includes placing a probe in contact with a surface of a material on a substrate and, with an initial force of 800 nano newtons or less; determining the location of the surface relative to an initial indentation depth for the initial force; increasing the force on the probe from the initial force to a maximum force greater than the initial force to generate a load curve; decreasing the force on the probe from the maximum force to the initial force to generate an unload curve, the maximum force selected such that the unload curve is independent of the presence of the substrate; and using the unload curve, determining a relationship between (i) the reduced modulus of the sample material and (ii) the ratio of probe penetration depth and the thickness of the layer.

19 Claims, 8 Drawing Sheets

(56) References Cited

U.S. PATENT DOCUMENTS

| | | |
|---|---|---|
| 6,609,428 B2 | 8/2003 | Hull |
| 6,662,631 B2 | 12/2003 | Baklanov et al. |
| 6,778,916 B2 | 8/2004 | Lee |
| 7,802,478 B2 | 9/2010 | Dill et al. |
| 2005/0084680 A1* | 4/2005 | Denes ............ B29C 59/14 428/411.1 |
| 2009/0193881 A1* | 8/2009 | Finnberg ............ B82Y 35/00 73/81 |
| 2011/0006406 A1* | 1/2011 | Urbanowicz ........ C23C 16/401 257/632 |
| 2012/0022802 A1* | 1/2012 | Sakuma ............ G01N 3/42 702/43 |
| 2014/0170424 A1* | 6/2014 | Honda ............ B05D 3/007 428/446 |
| 2016/0155988 A1* | 6/2016 | Kuroki ............ H01L 51/0097 257/40 |

OTHER PUBLICATIONS

Pharr, G. M.; Measurement of mechanical properties by ultra-low load indentation; Materials Science and Engineering A253 (1998); pp. 151-159.

Nay, et al.; Mechanical characterization of low-k dielectric materials using nonindentation; Microelectronic Engineering 75; Feb. 26, 2004; pp. 103-110.

Oliver, et al.; An improved technique for determining hardness and elastic modulus using load and displacement sensing indentation experiments; J. Matter. Res. vol. 7, No. 6, Jun. 1992; pp. 1564-1583.

Nagao, et al.; Achieving consistency of Young's modulus determination from nanoscale deformation of low-k films; Journal of Applied Physics 105, May 18, 2009; pp. 106104-1-106104-3.

* cited by examiner

DETERMINATION OF YOUNG'S MODULUS OF POROUS THIN FILMS USING ULTRA-LOW LOAD NANO-INDENTATION

BACKGROUND

The present invention relates to the field of Young's modulus measurement; more specifically, it relates to a method and system for determining the Young's modulus of porous thin films using ultra-low load nano-indentation.

In the semiconductor industry porous insulators are used as insulating layers in the wiring level of integrated circuits. In determining the suitability of porous insulators for use in integrated circuits, an accurate measurement of the Young's modulus of the insulator is a necessity. However, when such insulators are formed on silicon substrates it is fully accepted in the art that because of a "substrate effect", nano-indentation measurements of Young's modulus must be limited to an indentation depth of about 10% of the low-k sample thickness and that nano-indentation will overestimate Young's modulus for such materials by 100%. This renders the values so obtained virtually useless for suitability modeling purposes and requires extensive resources be spent on physical test structures. Accordingly, there exists a need in the art to eliminate the deficiencies and limitations described hereinabove.

BRIEF SUMMARY

A first aspect of the present invention is a method, comprising: placing a probe in contact with a surface of a layer of a sample material on a substrate with an initial force of 800 nano newtons or less; determining the location of the surface relative to an initial indentation depth for the initial force; increasing the force on the probe from the initial force to a maximum force greater than the initial force to generate a load curve of force versus probe penetration depth; decreasing the force on the probe from the maximum force to the initial force to generate an unload curve of force versus probe penetration depth, the maximum force selected such that the unload curve is independent of the presence of the substrate; and using the unload curve, determining a relationship between (i) a reduced modulus of the sample material and (ii) the ratio of probe penetration depth and the thickness of the layer.

A second aspect of the present invention is a method, comprising: placing a probe in contact with a surface of a porous material on a substrate located in an inert atmosphere; determining the location of the surface by applying a force of less than 800 nano newtons to the surface; determining the unload characteristics of the porous material using probe pressures selected such that (i) the unload characteristics of the porous material are substantially unaffected by the presence of the substrate and (ii) the probe simultaneously induces elastic and plastic deformation of the porous material; and performing data analysis of the unload characteristics to determine the relationship between (i) the modulus of the porous material and (ii) the ratio of contact depth to the thickness of the porous material.

A third aspect of the present invention is a computer program product for determining Young's modulus, the computer program product comprising a computer readable storage medium having program instructions embodied therewith, the program instructions executable by a computer, to cause the computer to: instruct a nano-indentation device to place a probe in contact with a surface of a layer of a sample material on a substrate with an initial force of 800 nano newtons or less; determine the location of the surface relative to an initial indentation depth for the initial force; instruct the nano-indentation device to increase the force on the probe from the initial force to a maximum force greater than the initial force and to generate a load curve of force versus probe penetration depth; instruct the nano-indentation device to decrease the force on the probe from the maximum force to the initial force and to generate an unload curve of force versus probe penetration depth, the maximum force selected such that the unload curve is independent of the presence of the substrate; and using the unload curve, determining a relationship between (i) a reduced modulus of the sample material and (ii) the ratio of probe penetration depth and the thickness of the layer.

These and other aspects of the invention are described below.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings, wherein:

DETAILED DESCRIPTION

The embodiments of the present invention utilize a novel combination of ultra-low load nano-indentation and newly developed algorithms to obtain Young's modulus values for porous low-k semiconductor insulators that do not require limitation of the indentation depth and show no substrate effect.

In the miniaturization of semiconductor electronics, the metal lines that carry signals to microprocessors get ever closer, increasing parasitic capacitive losses especially when operating at frequencies in the range of hundreds of MHz. A standard in the industry today to reduce these losses is to insert between the conducting elements materials of low dielectric constant ('low-k'), lower than silicon dioxide, which has been the insulating material of choice for almost three decades. Chemical modification of the silica network, first by the introduction of fluorine and eventually by the addition of carbon, has been adopted as a path to introducing low-k materials in manufacturing. Using this strategy, the dielectric constant can be desirably lowered to 2.7-2.6 as a result of a decrease in network connectivity and hence a decrease in material density. These two characteristics have a strong impact on mechanical properties. For example, a reduction in dielectric constant (k) of one-third is accompanied by an order of magnitude decrease in Young's modulus (E) when going from $SiO_2$ (k=4.0, E=72 GPa) to carbon-doped silicon oxides (k=2.7, E=7-10 GPa). By controlling porosity, carbon-doped oxides offer the potential for continued reduction of dielectric constant without changing elemental composition. The addition of nanometer-sized pores to existing low-k materials, while commonly embraced as the only manufacturing-compatible way to access the desired ultralow-k regime of k less than 2.4, introduces a number of new integration issues.

Most importantly, the mechanical strength of the dielectric silicon oxides, already degraded by a decrease in network connectivity in carbon-doped oxides, is further reduced by increasing porosity. This leads to films that crack on curing or during mechanically demanding processing and packaging steps. For this reason, accurate techniques are essential for determining the mechanical properties of these ultralow-k thin films at the thicknesses used for integration into devices and on diverse substrates. Accurate Young's modulus values also strengthen the modeling input for finite element analysis of materials in future chip design.

The embodiments of the present invention perform nano-indentation using ultra-low maximum loads. In one example, the maximum load is between 3 μN and 25 μN. In one example, the maximum load is less than 25 μN. In one example, the maximum load is less than 10 μN. The embodiments of the present invention perform nano-indentation on materials having very low dielectric constants. In one example, the materials have a dielectric constant of less than or equal to 4.0. In one example, the materials have a dielectric constant of less than or equal to 2.7. In one example, the materials have a dielectric constant of less than or equal to 2.3. The embodiments of the present invention perform nano-indentation on very thin layers of material on a substrate. In one example, the layer of material has a thickness of less than or 1000 nm. In one example, the density of the material is less than 1 g/cm$^3$. While the embodiments of the present invention are illustrated using porous low-k materials, the invention may be used on other materials, such as plastic and/or elastic deformable materials.

Figure 1:
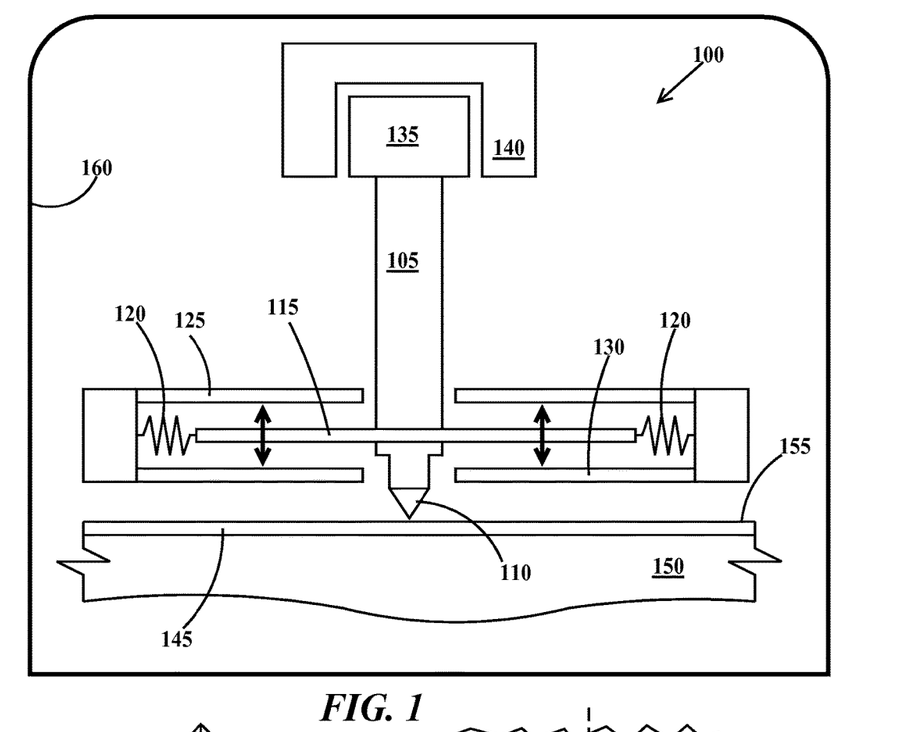
FIG. 1 is a schematic diagram of a nano-indentation tool.

FIG. 1 is a schematic diagram of a nano-indentation tool. In FIG. 1, an exemplary nano-indentation tool 100 includes a probe 105 having a diamond tip 110 connected to a lower end of probe 105. Probe 105 is supported by a beam 115 connected to springs 120 to allow vertical up and down movement of probe 105. Beam 115 is positioned between an upper plate 125 and a lower plate 130. Beam 115, upper plate 125 and lower plate 130 comprise a capacitive displacement gauge. Movement of beam 115 relative to upper plate 125 and lower plate 130 causes a change in capacitance/voltage, which is then converted to a vertical displacement. An electromagnetic coil 135 is attached to the upper end of rod 105 inside of a magnet 140. Varying the voltage on coil 135 allows control of the vertical position of probe 105. A motorized stage 150 is supplied to hold a sample 145. By adjusting the current on coil 135, tip 110 may be forced into the surface 155 of sample 145 and the depth measured by the capacitive displacement gauge. Nano-indentation tool 100 is contained in an environmental chamber 160 that may be purged and filled with a dry inert gas (in one example, dry nitrogen where dry is defined as less than 2 ppm water). The low-k sample being measured should be dry (e.g., containing less than 1% by weight of water) which may be accomplished, for example, by placing the low-k sample in dry nitrogen for several hours. It is a feature of the preferred aspects of the present invention that nano-indentation measurements be performed in a dry inert atmosphere because moisture will adversely effect the accuracy of the data obtained.

As the load (force) is increased on the indenter at a set rate the indenter tip penetrates further into sample until a set maximum force is reached. At this point the load is held constant for a set period of time and then the load is decreased at a set rate. A record of the force and indentation displacement is made and then the area of the indent formed is determined using the geometry of the indenter tip. The record of the force and indentation displacement can be plotted to create a load-displacement curve. These curves and the data are used to determine mechanical properties of the sample. In one example, the maximum penetration of the indenter tip into the low-k material is between 0.1% and 60% of the thickness of the sample being measured. In one example, the maximum penetration of the indenter tip into the low-k material is greater than or equal to 10 nanometers. This determination is discussed infra with respect to FIG. 4.

Figure 2:
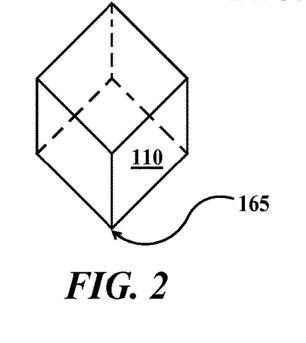
FIG. 2 is a diagram of the tip of the nano-indentation of FIG. 1.

FIG. 2 is a diagram of tip 110 of the nano-indentation of FIG. 1. In FIG. 2, diamond tip 110 is a cube (the diamond crystal structure is a face centered cube). It is mounted so a corner of the cube acts as the point 165 that is forced into the sample. It is a feature of the present invention that a cube corner tip, preferably diamond, be used.

Figure 3:
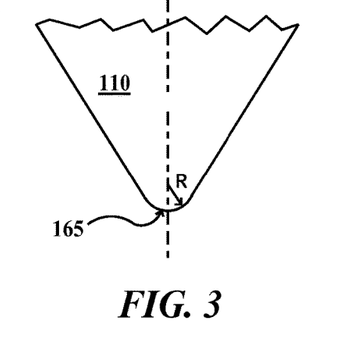
FIG. 3 is a diagram of the point of the tip of FIG. 2 according to an embodiment of the present invention.

FIG. 3 is a diagram of the point 165 of tip 110 of FIG. 2 according to an embodiment of the present invention. In FIG. 3, point 165 has a radius R. It is a feature of a preferred embodiment of the present invention that R has a value equal to less than 40 nm. Nano-indentation will generate a load/unload curve as discussed in infra with respect to FIG. 5.

Figure 4:
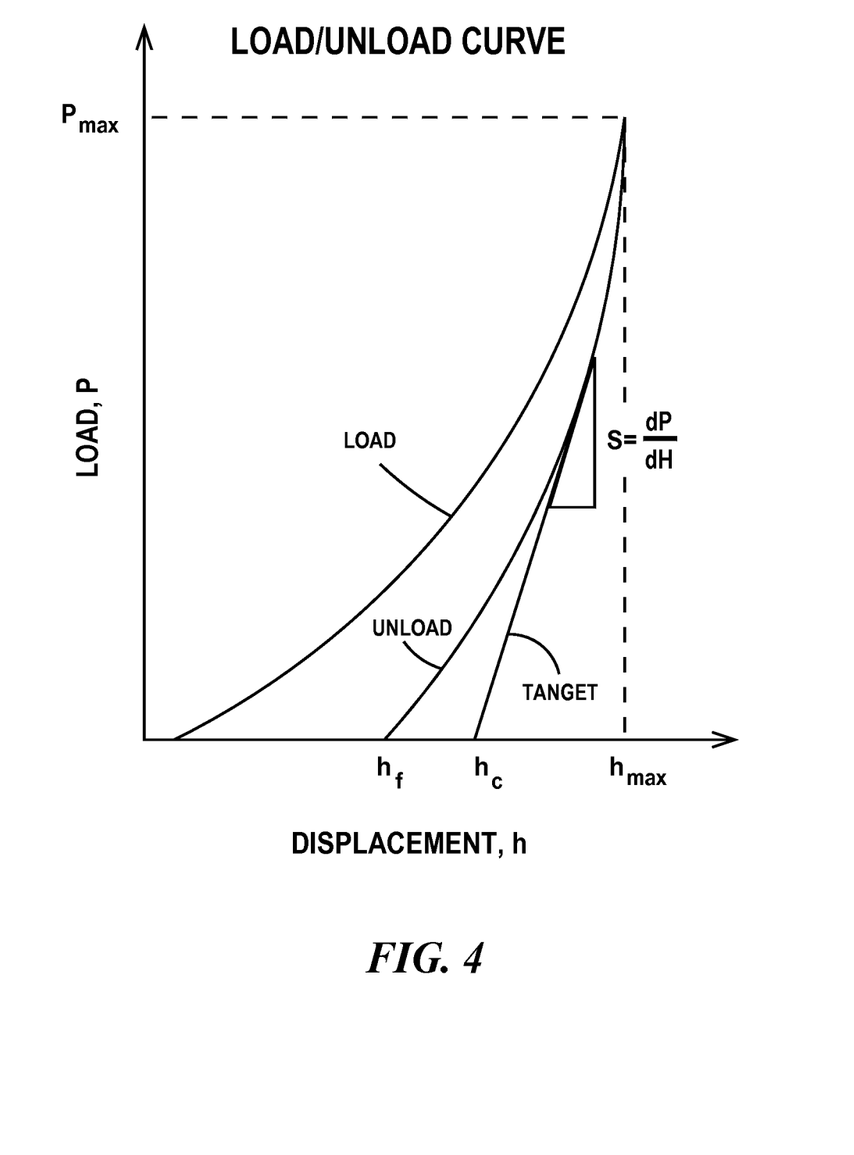
FIG. 4 is an exemplary load vs. displacement curve generated by the nano-indentation tool illustrating regions used to calculate Young's modulus according to an embodiment of the present invention.

FIG. 4 is an exemplary load vs. displacement curve generated by the nano-indentation tool illustrating regions used to calculate Young's modulus according to an embodiment of the present invention. In FIG. 4, load (P) is plotted vs. displacement. Load is the force placed on the tip of the nano-indenter and displacement is the depth of the tip into the sample. As the load on the tip increases, the load curve increases to a maximum load, $P_{max}$, at a maximum displacement, $h_{max}$. As the load is then decreased (unload) the displacement decreases to final displacement $h_f$. The nano-indenter generates a tangent to the slope, which intercepts the displacement axis at a contact depth $h_c$. The contact depth is the penetration depth of the probe tip into the sample measured from the sample surface.

Load P is related to displacement h by equation (1):

$$P = \alpha(h-h_f)^m \quad (1)$$

where

P is the load;

$h_f$ is the final displacement; and

α and m are determined by software using nonlinear convergence of unload curve data points of the 99% to 50% portion of the unload curve.

The derivative of load with respect to displacement of this tangent line is the contact stiffness, S, and is given by equation (2):

$$S = \frac{dP}{dh} \quad (2)$$

where:
S is the stiffness;
P is load; and
h is displacement.

The differentiation is performed at $h_{max}$ (in practice, at 99% of $h_{max}$).

The reduced modulus is related to the stiffness and the area of the indentation by equation (3):

$$E_r = \frac{1}{\beta} \frac{\sqrt{\pi}}{2} \frac{S}{\sqrt{A_p(h_c)}} \quad (3)$$

where:
$E_r$ is the reduced modulus;
β is a constant (generally equal to 1 for non-metallic samples);
S is the stiffness; and
$A_p(h_c)$ a function for the area of the indentation at the contact depth $h_c$.

The area function is represented by equation (4):

$$A = C_0(h_c)^2 + C_1(h_c) + C_2(h_c)^{1/2} \quad (4)$$

where
$h_c$ is the contact depth,
$C_0$, $C_1$ and $C_2$ are fitting coefficients determined by fitting the parabolic shape.

Young's modulus $E_s$ can be determined from equation (5):

$$\frac{1}{E_r} = \frac{(1 - v_i^2)}{E_i} + \frac{(1 - v_s^2)}{E_s} \quad (5)$$

where:
$E_r$ is the reduced modulus from equation (2);
$E_i$ is the indenter modulus (1140 GPa for diamond);
$v_i$ is the indenter Poisson's ratio (0.07 for diamond); and
$v_s$ is the sample Poisson's ratio (0.25 was used).

Figure 5:
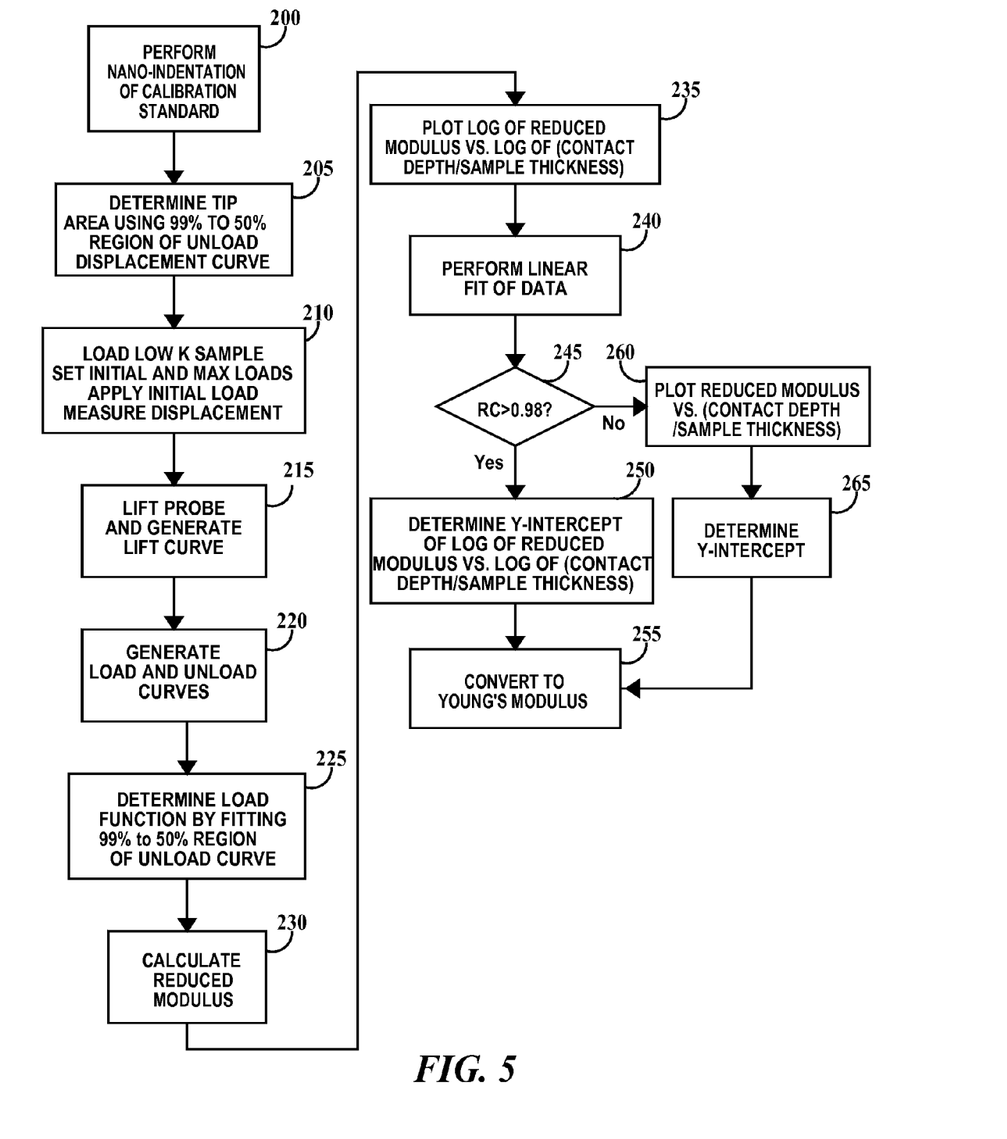
FIG. 5 is a flowchart of the method for determining Young's modulus according to an embodiment of the present invention.

FIG. 5 is a flowchart of the method for determining Young's modulus according to an embodiment of the present invention. Steps 200 through 210 are calibration steps. Steps 215 through 225 are low-k sample measurement steps, and steps 230 through 265 are Young's modulus calculation steps.

In step 200, the nano-indentation of a standard (e.g., quartz having a Young's modulus of 70 GPa) is performed. In the present example, the standard sample is quartz on silicon and the tip is a diamond corner having a radius equal to or less than 40 nm. In step 205, the values for a and m of equation (1) are determined using the 99% to 50% region of the unload curve obtained from the quartz standard. Then the area of the tip is determined using equations (2) and (3). In step 210, a low-k sample to be measured is placed in the nano-indenter and an initial load and a maximum load are set. The initial load is selected to balance the requirements of minimum surface perturbation with sufficient loads to stabilize contact of the tip to the sample. In one example, the initial load is 700 nano newtons (nN). In one example, the initial load is equal to less than 800 nN. In one example, the maximum load is less than 50 micro newtons (μN). In one example the maximum load is equal to less than 25 μN. The initial load is applied to the low-k sample and a first displacement value is measured. However, the first displacement value is not relatable to the actual surface of the low-k sample.

In step 215, the probe is lifted away from the low-k sample and a lift curve to the surface at zero load is generated. (See the lower curve 285 from point 275 to point 280 of FIG. 6). In step 220, the load is then increased at a fixed rate from a zero load to the maximum load. A second displacement value is obtained as the load is increased. After a hold at the maximum load, the load is reduced at a known rate until the initial load is reached again. The difference between the first and second displacement values is used to generate a displacement correction to the load and unload curves so the load and unload curves reflect displacements from the actual surface. The load and unload curves start and finish at the initial load (see point 275 of FIG. 6).

In step 225, the values for a and m of equation (1) are determined using the 99% to 50% region of the unload curve obtained from the low-k sample using equations 1. In step 230, the reduced modulus is calculated using equations (2) and (3) and the area obtained in step 205. In step 235, the log of the reduced modulus is plotted vs. the log of (contact depth/sample thickness) and in step 240 a linear fit and a regression coefficient of the data points for the sample is performed. Note the term "(contact depth/sample thickness)" is read as the ratio of contact depth to sample thickness or contact depth divided by sample thickness. In one example, the linear fit is performed using a least squares fit.

In step 245 it is determined if the regression coefficient is greater than 0.98. If the regression coefficient is greater than 0.98 the method proceeds to step 250. The value 0.98 is exemplary. In another example it is determined if the regression coefficient is greater than 0.96. If the regression coefficient is greater than 0.96 the method proceeds to step 250. In step 250, the log of reduced modulus versus the log of (contact depth/low-k sample thickness) is plotted and the Y-intercept at 0.01 (1%) of the log of (contact depth/low-k sample thickness). Next, in step 255, the reduced modulus is converted to Young's modulus using equation (5).

Returning to step 245, if the regression coefficient is ≤0.98 the method proceeds to step 260. Again the value 0.98 is exemplary. In step 260, the reduced modulus versus (contact depth/sample thickness) is plotted. In another example, if the regression coefficient is ≤0.96 the method proceeds to step 260. In step 265, the Y-intercept of the linear reduced modulus is determined and the method proceeds to step 255.

Figure 6:
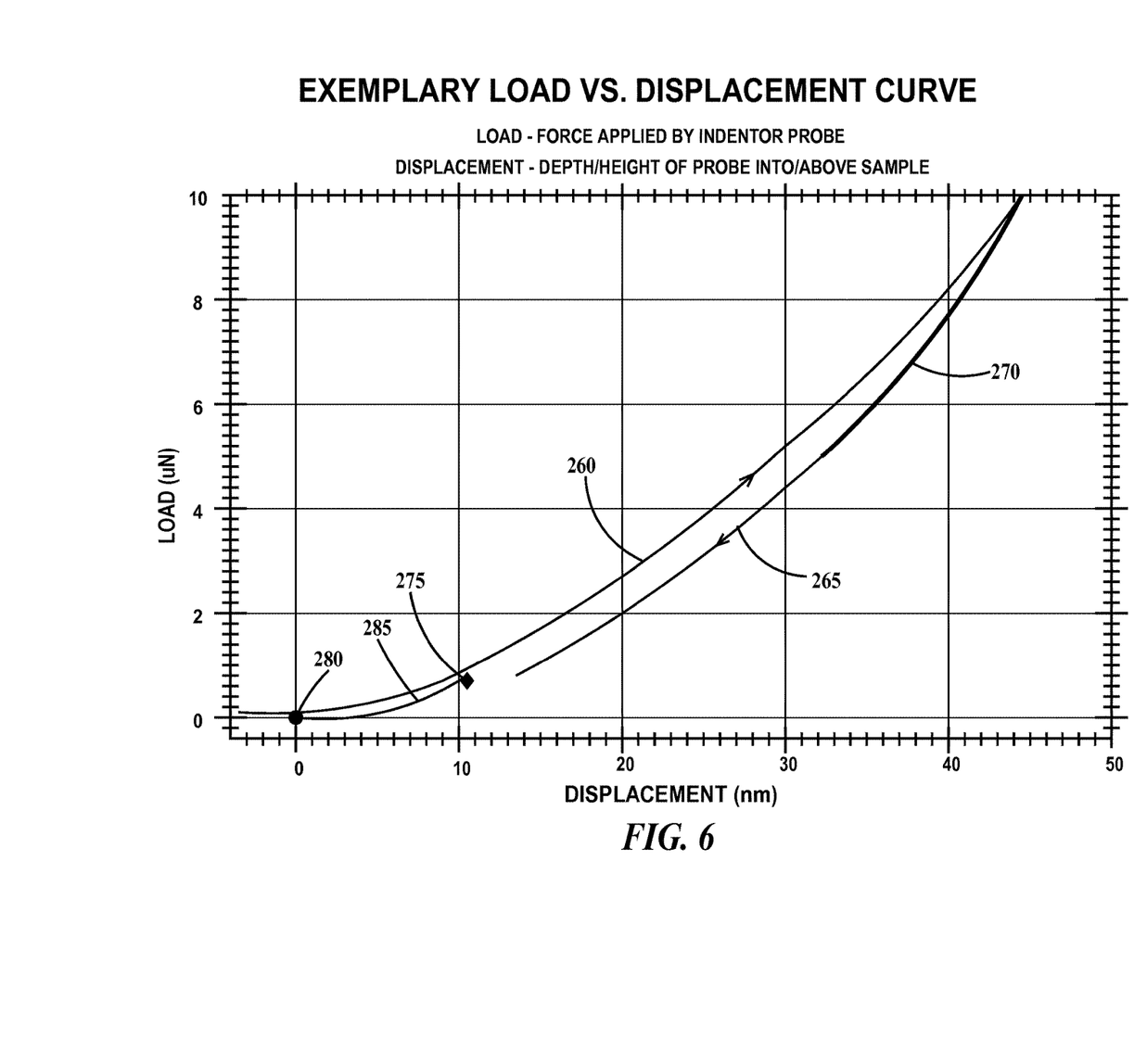
FIG. 6 is a typical plot of load as a function of displacement according to embodiments of the present invention.

FIG. 6 is a typical plot of load as a function of displacement. Curve 260 is the load curve and curve 265 is the unload curve. The heavy line region 270 is the 99% to 50% portion of unload curve 265 used in the calculation of the Young's modulus. The initial point of contact 275 is at about 700 μN with an initial indentation depth of about 10 nm. Curve 285 is the lift curve.

EXPERIMENTAL

Synthesis of Low-k Dielectric Films

The spin-on porous low-k dielectric films of this study were synthesized from a mixture of a material that forms a continuous organosilicate matrix and a material that forms the pores in the matrix, the porogen. Porosity was systematically varied by varying the mass ratio of porogen to matrix in the starting mixture. The organosilicate matrix precursor was a copolymer of methyl trimethoxysilane and tetra-ethoxyorthosilicate with an approximate mol. wt. of 2,000 Daltons. The porogen was a propylene glycol-based polyol with a molecular weight of 6,000 Daltons. Eight different mass ratios (Table 1, Samples A, B, C, D, E, F, G and H) of the two components were prepared as solutions in propylene glycol mono-n-propyl ether solvent and spun onto silicon wafers. A heating cycle (ramp from 25° C. to 425° C. over 1 h) accomplished the next steps of (1) phase separating the two components and cross-linking the organosilicate in the 150-200° C. range and (2) eliminating the porogen as the temperature further increased to 425° C. The eight resulting porous organosilicate films (600 nm-800 nm thick) were then characterized for thickness and density using x-ray reflectivity.

Nano-Indentation

Nano-indentation measurements were performed on a commercial nano-indenter, Hysitron Model TI-950 having an enclosure and fitted with a diamond cube corner probe of 40 nm end radius. To eliminate adsorbed moisture that could complicate measurements of mechanical properties by causing effects such as adhesion, nano-indentation was carried out under a positive pressure of dry nitrogen in the closed indenter enclosure. Freshly loaded samples were allowed to equilibrate with dry nitrogen for about 12 hours, also achieving thermal equilibrium. The diamond cube corner probe was calibrated on a quartz sample with a modulus of 70 gigapascals (GPa). Quartz was chosen because it undergoes a plastic deformation on indentation, providing true profiles of the diamond indenter tip shape for use in calculating contact areas for silicate film indentation. Atomic force microscope (AFM) images of the about 60 nm shallow indents into quartz revealed that the residual deformation could be fit by a parabolic surface, justifying the use of only three coefficients to fit the tip area function instead of the customary six or eight coefficients. See equation (3) supra. The indents into low-k samples were also shallow (less than 60 nm contact depth as measured by AFM and representing less than 10% of the total low-k sample thicknesses used in this study. A graph of modulus as a function of contact depth was then plotted for the series of loads for each sample.

Eight different low-k samples were prepared (see Table 1). The indents into low-k samples were less than 60 nm contact depth as measured by AFM, representing less than 10% of the total low-k sample thicknesses used in this study (see Table 1). In a preload indentation step, the indenter probe approached the low-k sample surface with a set point load of 700 nN chosen to balance the requirements of minimal surface perturbation with sufficient load for stable contact. Each low-k sample was indented with a series of eight maximum forces of 25 µN, 20 µN, 15 µN, 12.5 µN, 10 µN, 7.5 µN, 5 µN and 3 µN. For each load, seven independent indents were performed on the surface at least 10 µm apart from each other. This yielded 56 data points per low-k sample. The load function was comprised of a sequence of three steps: load, hold, and unload. The maximum force was reached in 5 seconds in the load step; the maximum force was held for 2 seconds in the hold step; and the force was ramped down to 700 nN in 5 seconds in the unload step. The upper half (99% to 50%) of the unload curve (see FIG. 7 and discussion infra) was fitted with the above-mentioned tip area function to yield a contact stiffness, used in calculating the reduced modulus ($E_r$) from classic Oliver-Pharr equations.

Figure 7:
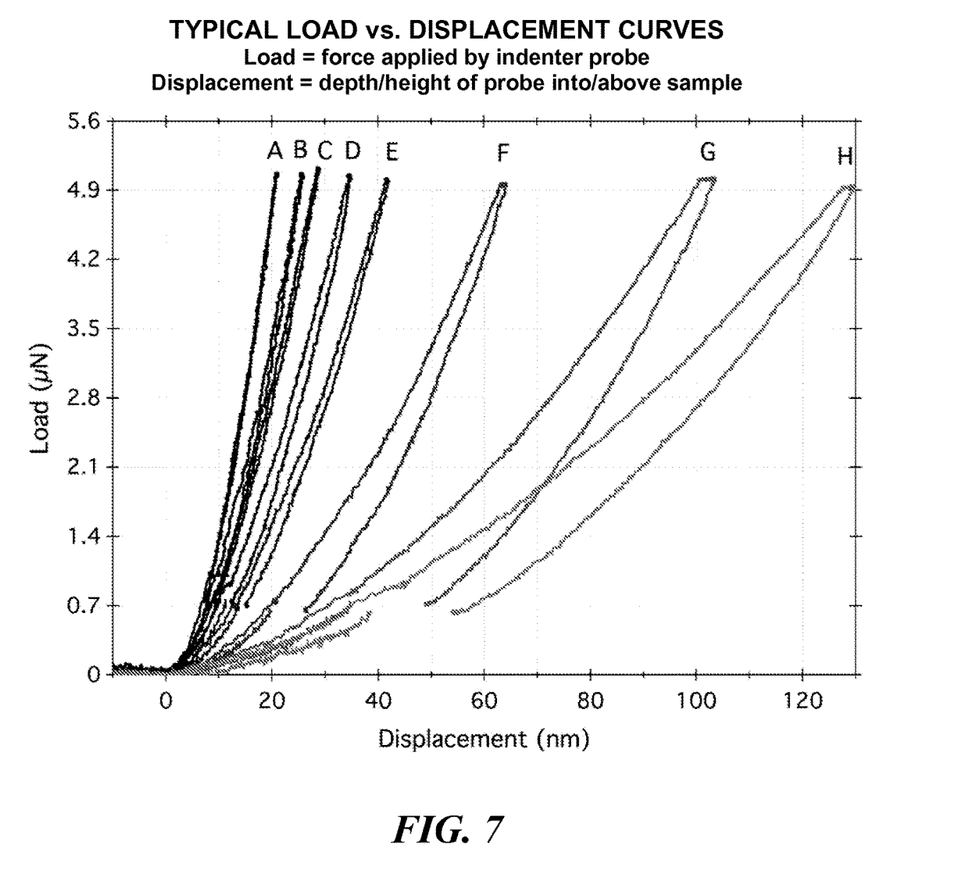
FIG. 7 illustrates Young's modulus vs. contact depth curves for the eight low-k samples prepared.

FIG. 7 is a schematic load vs. displacement curve illustrating typical load vs. displacement curves for the eight low-k samples prepared. In FIG. 7, a typical load displacement curve is shown for one measurement cycle of each of the eight low-k samples prepared at the 5 µN maximum load. The different samples labeled A, B, C, D, E, F, G and H correspond to the same samples in FIGS. 8 and 9 and Table I.

X-Ray Reflectivity (XRR)

Specular X-ray reflectivity was used to measure low-k sample thickness and density with a Panalytical X'Pert Pro MRD diffractometer employing a ceramic x-ray tube ($\lambda$=0.154 nm) and a high-resolution goniometer (resolution±0.0001°). The critical angles from the reflectivity data were obtained from the peak position of $Iq^4$-vs.-q plots (q=4π/λ sin Θ), where λ is the wavelength and Θ is the grazing incident angle of the x-ray beam.

Surface Acoustic Wave Spectroscopy (SAWS)

SAWS is a well established and accepted technique for low-k dielectric measurements. Elastic moduli were measured by SAWS on a Fraunhofer LaWave spectrometer. Acoustic waves were generated by a nitrogen-pulsed laser ($\lambda$=337 nm, pulse duration=0.5 nanoseconds) and detected with a piezoelectric polymer-based transducer. Fitting the measured surface wave velocity as a function of frequency with a theoretical dispersion curve and factoring in the sample thickness and density obtained from XRR measurements yielded a reduced elastic modulus.

Results and Discussion

Advantageous aspects of this nano-indentation study were: (1) Use of dry nitrogen ambient to eliminate the effects of moisture both on the surface as well as in the pores; (2) The choice of ultra-low, maximum indentation loads (3 µN to 25 µN) to minimize and eliminate the so called substrate effect; (3) Use of sharp (40 nm end radius) cube-corner probe to cause elastic and plastic deformation of the sample in order to extract the hardness and Young's modulus information; and (4) Methods of data analysis. The indenter operated in a 'load control' mode where motion of the probe was constrained such that the load was controlled precisely and the sample was free to deform under the action of the applied load. While applying the load, the system continuously captured the probe's deformation into the sample, thus yielding a load-vs.-displacement graph.

The following protocol for generating the curves of FIG. 6 and FIG. 7 was used: The sample surface was located using a 700 nN initial load. Next, the probe was then retracted (lifted) by 50 nm from the established surface and then re-approached to perform the load function (load, hold and unload, vide supra).

At the low loads used, the lift protocol is critical for minimizing the error in determining the indentation contact depth. Lifting the probe away from the sample serves two purposes: (1) to determine the point of zero load and zero displacement, where the load and unload curves converge (280) after the initial 700 nN set point load and (2) to reveal a documentable deformation caused by the initial set point load.

Once the initial approach was complete, the indentation process was carried out in the three steps (of load, hold and unload) with the following observations: (1) Abrupt increases in the displacement for the same applied load were not detected during loading (or unloading), indicating the use of a cube-corner probe at ultralow loads avoided cracking and phase-transformations observed at larger loads; (2) While holding the force at 10 uN for 2 seconds, the displacement was relatively unchanged for samples A through E, indicating a negligible amount of sample creep but was substantial for samples F through G. The creep of samples F through G is seen in the displacement of the unload curve from the load curve at the 5 μN load in FIG. 6; (3) At the end of the unload curve plastic deformation results in the unload curves not falling on top of each other.

Figure 8:
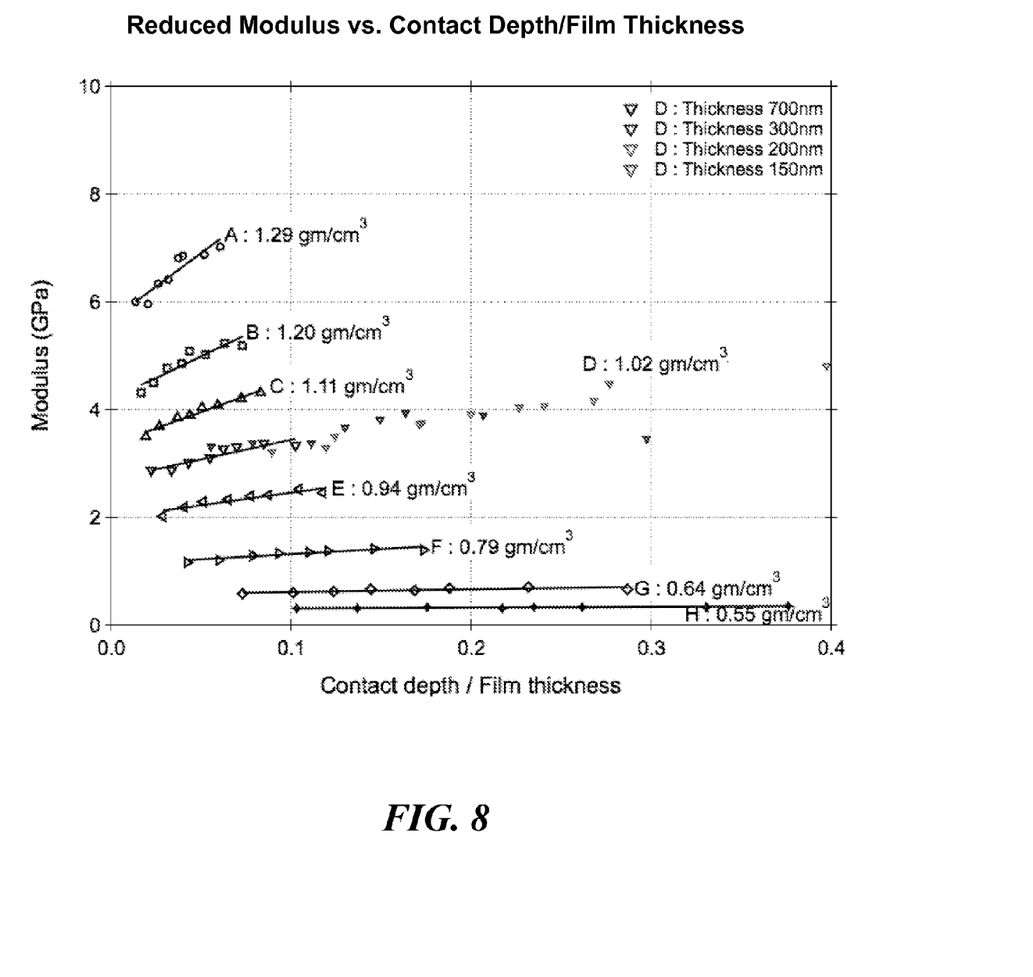
FIG. 8 plots reduced modulus vs. (contact depth/low-k sample thickness) curves generated for the eight low-k samples prepared.
Figure 9:
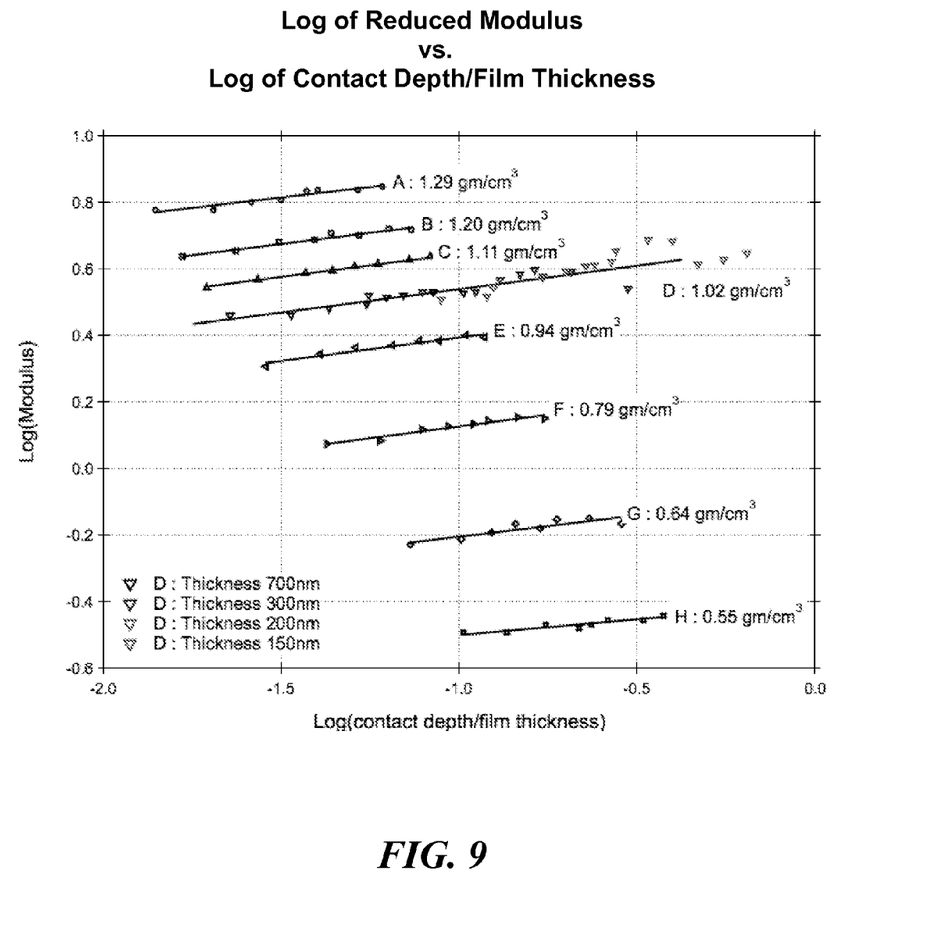
FIG. 9 plots the log of the reduced modulus vs. log (contact depth/low-k sample thickness) generated for the eight samples prepared.

The load-hold-unload process was repeated on each sample seven times at each load for statistical significant sampling. With eight test loads (25 μN, 20 μN, 15 μN, 12.5 μN, 10 μN, 7.5 μN, 5 μN and 3 μN), each sample underwent acquisition of 56 load-vs.-displacement curves. After each sample, load vs. displacement curves were recorded from a quartz calibration sample to confirm the health of the indenter probe. Reduced modulus values were calculated from the force-vs.-displacement curves of FIG. 7 using the Oliver-Pharr model. FIG. 8 plots reduced modulus vs. (contact depth/low-k sample thickness) curves generated for the eight low-k samples prepared. Contact depth/low-k sample thickness should be read as contact depth divided by low-k sample thickness. FIG. 9 plots the log of the reduced modulus vs. log (contact depth/low-k sample thickness) generated for the eight samples prepared. FIG. 8 uses a linear analysis method and FIG. 9 uses a log-log analysis method of the embodiments of the present invention. Reduced Young's moduli may be converted to Young's moduli using equation (5). It is preferred to use the same algorithm base for both the reduced modulus as well as (contact depth/low-k sample thickness). Each curve of FIGS. 8 and 9 represents one of samples A through H. Each of the eight points on each curve represents a different maximum load in the order 25 μN, 20 μN, 15 μN, 12.5 μN, 10 μN, 7.5 μN, 5 μN and 3 μN from left to right. Each point is made up of seven measurements. At least three measurements are required. The linear fit was performed using all 56 data points.

TABLE 1

| Sample | Porogen % | Density gm/cm$^3$ | Thickness nm | E (SAWS) GPa | E (linear) GPa | E (loglog) GPa |
|---|---|---|---|---|---|---|
| A | 0 | 1.286 | 586.1 | 4.84 | 5.32 | 5.09 |
| B | 5 | 1.197 | 599.9 | 3.74 | 3.95 | 3.8 |
| C | 10 | 1.106 | 618.3 | 2.90 | 3.15 | 2.99 |
| D | 15 | 1.017 | 625.3 | 2.19 | 2.56 | 2.29 |
| E | 20 | 0.940 | 641.8 | 1.71 | 1.88 | 1.69 |
| F | 30 | 0.789 | 686.7 | 0.86 | 1.07 | 0.9 |
| G | 40 | 0.642 | 715.4 | 0.44 | 0.54 | 0.43 |
| H | 50 | 0.551 | 736.6 | 0.14 | 0.29 | 0.24 |
| D | 15 | 1.017 | 300 | 2.19 | >3 | 2.27 |
| D | 15 | 1.017 | 200 | 2.18 | >3 | 2.23 |
| D | 15 | 1.017 | 150 | 2.19 | >3 | 2.24 |

Table 1 shows, for each low-k sample prepared and measured, the porogen percentage, the density of the material, the thickness of the film measured, the SAWS Young's Modulus as a standard, the Young's Modulus calculated using linear analysis and the Young's Modulus using log-log analysis.

In the log-log analysis method irrespective of the porogen content, the slope of the lines are all 0.13 (+/−0.015). This is an unexpected result because linear analysis does not yield such a result and in fact yields a slope that is a function of sample density. Thus, on a log-log plot it is possible, for each low-k sample, to determine an intercept on the Y-axis where the log (contact depth/low-k sample thickness) is about 1%. This intercept on the Y-axis is the log(modulus) from which modulus values can be easily calculated. The error in modulus determination is less than 5% for all the values of porogen content. This is the first time, using an indentation based technique, that the measured moduli match nearly exactly those measured using an established technique such as surface acoustic wave spectroscopy. A plot of the log of the modulus (GPa) determined using log-log analysis (FIG. 9) vs. low-k sample density (g/cm$^3$) virtually superimposes with SAWS data for samples A through G. By contrast, a plot of the log of the modulus (GPa) determined using conventional linear analysis (FIG. 8) vs. low-k sample density (g/cm$^3$) show consistently low moduli compared to SAWS data with errors in the 20% to 50% range. This is shown in Table 2.

TABLE 2

| Sample | Porogen % | Density (gm/cm$^3$) | Thickness (nm) | E (SAWS) (GPa) | E (NI) (GPa) (conv.) | E (NI) (GPa) (Present) |
|---|---|---|---|---|---|---|
| A | 0 | 1.286 | 586.1 | 4.84 | 5.32 | 5.09 |
| B | 5 | 1.197 | 599.8 | 3.74 | 3.95 | 3.8 |
| C | 10 | 1.106 | 618.3 | 2.90 | 3.15 | 2.99 |
| D | 15 | 1.017 | 625.3 | 2.19 | 2.56 | 2.29 |
| E | 20 | 0.940 | 641.8 | 1.71 | 1.88 | 1.68 |
| F | 30 | 0.789 | 686.7 | 0.86 | 1.07 | 0.9 |
| G | 40 | 0.642 | 715.4 | 0.44 | 0.54 | 0.43 |
| H | 50 | 0.551 | 736.6 | 0.14 | 0.29 | 0.24 |
| D | 15 | 1.017 | 300 | 2.19 | >3 | 2.27 |
| D | 15 | 1.017 | 200 | 2.18 | >3 | 2.23 |
| D | 15 | 1.017 | 150 | 2.19 | >3 | 2.24 |

Table 2 shows, for each low-k sample prepared and measured, the log of SAWS Young's Modulus as a standard, the log of the Young's Modulus calculated using linear analysis and the log of the Young's Modulus using log-log analysis. For the H sample it is believed that SAWS is underestimating the Young's modulus because that point is a flier in both sets of data.

Thus, the graph reveals that when the porous samples are indented with pressures that cause elastic and plastic deformation there is indeed a regime where it is possible to substantially reduce, or as in our case, completely eliminate the substrate effect. The ability to eliminate the substrate effect is an unexpected result. Additionally, the measurement of Young's modulus by the log-log method was found not to be a function of thickness.

It is speculated that the log-log analysis method provides such accurate results, because with a sharp probe (especially when both elastic and plastic deformation occurs) the pores under the tip collapse resulting in a denser material. It is reasonable to assume that the pore collapse does not result in the formation of a solid with regular lattice structure. Instead a denser version of the same porous material is formed. Thus the slope of the log (measured modulus) vs. log (depth-to-low-k sample thickness) is essentially a straight line. Using indentation it is possible to locally create denser versions of the same porous material. One of the results of this densification is the fact that the strain is locally relaxed as opposed to being propagated all the way to the substrate.

Nano-indentation analysis was performed on porous materials that exhibit a linear increase in modulus as function of density. For those materials, a simple linear-linear analysis was sufficient to measure modulus values that were equivalent to those measured with SAWS. However the requirements of performing the measurements in dry nitrogen ambient, use of sharp cube-corner probe, as well as ultra-low loads was essential for accuracy.

In order to test the requirement to create elastic and plastic deformation, nano-indentation was performed using a Berkovich probe with an end radius of about 100 nm and included angle of 120 degrees. With all other conditions being met (clean dry environment as well as ultra-low loads) it was not possible to obtain a reasonable value for the modulus of porous materials. Even though the total displacement into the sample was comparable, the modulus values obtained with a Berkovich probe were highly overestimated because the probe tip geometry did not allow plastic deformation at low forces.

Generally, the method described herein with respect to a method for determination of Young's modulus of porous thin films using ultra-low load nano-indentation is practiced with a general-purpose computer and the methods described supra in the flow diagrams of FIG. 1 may be coded as a set of instructions on removable or hard media for use by the general-purpose computer.

Figure 10:
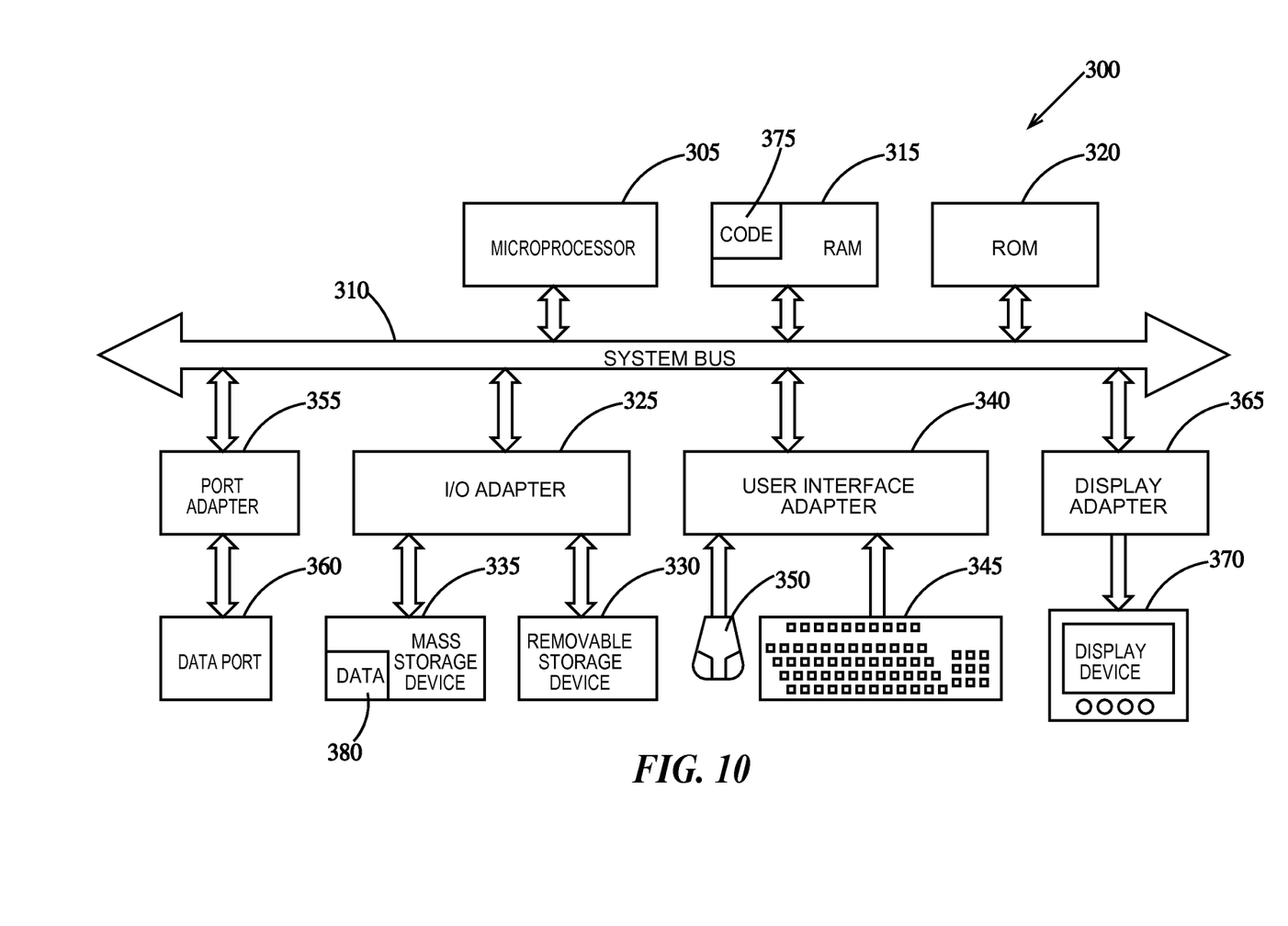
FIG. 10 is a schematic block diagram of a general-purpose computer.

FIG. 10 is a schematic block diagram of a general-purpose computer. In FIG. 10, computer system 300 has at least one microprocessor or central processing unit (CPU) 305. CPU 305 is interconnected via a system bus 310 to a random access memory (RAM) 315, a read-only memory (ROM) 320, an input/output (I/O) adapter 325 for connecting a removable data and/or program storage device 330 and a mass data and/or program storage device 335, a user interface adapter 340 for connecting a keyboard 345 and a mouse 350, a port adapter 355 for connecting a data port 360 and a display adapter 365 for connecting a display device 370. RAM 315 includes code 375 for storing application software and other software and mass storage device 335 includes document and file storage data 380 which includes documents and databases created by the user or software applications. The nano-indentation tool may be connected to computer 300 through data port 360. The measurements stored in mass storage device 335 and converted to Young's Modulus measurements by algorithms stored in code 375 and run on microprocessor 305. The Young's modulus measurements may in turn be stored in mass storage device 335, displayed on display device 370, written to removeable storage device 330, or sent to a printer (not shown).

ROM 320 contains the basic operating system for computer system 300. The operating system may alternatively reside in RAM 315 or elsewhere as is known in the art. Examples of removable data and/or program storage device 330 include magnetic media such as floppy drives and tape drives and optical media such as CD ROM drives. Examples of mass data and/or program storage device 335 include electronic, magnetic, optical, electromagnetic, infrared, and semiconductor devices. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. In addition to keyboard 345 and mouse 350, other user input devices such as trackballs, writing tablets, pressure pads, microphones, light pens and position-sensing screen displays may be connected to user interface 340. Examples of display devices include cathode-ray tubes (CRT) and liquid crystal displays (LCD).

A computer program with an appropriate application interface may be created by one of skill in the art and stored on the system or a data and/or program storage device to simplify the practicing of this invention. In operation, information for the computer program created to run the present invention is loaded on the appropriate removable data and/or program storage device 330, fed through data port 360 or typed in using keyboard 345.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, tool (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing tool to produce a machine, such that the instructions, which execute via the processor of the computer or other programmable data processing tool, create means for implementing the functions/acts specified in the flowchart and/or block diagram block or blocks. These computer readable program instructions may also be stored in a computer readable storage medium that can direct a computer, a programmable data processing tool, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing tool, or other device to cause a series of operational steps to be performed on the computer, other programmable tool or other device to produce a computer implemented process, such that the instructions which execute on the computer, other programmable tool, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Therefore, the embodiments of the present invention provide a method and system for accurate determination of the Young's modulus of very thin porous films using ultra-low load nano-indentation with no substrate effect and no 10% of total thickness indentation depth limit.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
   placing a probe, of a nano-indenter, in contact with a surface of a layer of a sample material on a substrate with an initial force of 800 nano newtons or less;
   determining an area function of a tip of said probe on a layer of a standard material on said substrate;
   measuring a low-k sample placed in said nano-indenter for measurement;
   selecting an initial load, associated with said initial force, configured to balance requirements of a minimum surface perturbation with loads for stabilizing contact of the tip with respect to said low-k sample;
   applying said initial load to said low-k sample;
   measuring, based on said applying, a first displacement value;
   selecting a maximum load associated with said initial load;
   determining a location of said surface relative to an initial indentation depth for said initial force;
   increasing the force on said probe from said initial force to a maximum force, associated with said maximum load, greater than said initial force to generate a load curve of force versus probe penetration depth; S/N: 14/607,291 2
   decreasing the force on said probe from said maximum force to said initial force to generate an unload curve of force versus probe penetration depth, said maximum force selected such that the unload curve is independent of the presence of said substrate; and
   using said unload curve, determining a relationship between (i) a reduced modulus of said sample material and (ii) a ratio of probe penetration depth and a thickness of said layer;
   using said area function and said unload curve to extract said reduced modulus; and
   using said reduced modulus, a Poisson's ratio of said sample material, a modulus of said standard material, and a Poisson's ratio of said standard material to determine a Young's modulus of said sample material.

2. The method of claim 1, wherein said relationship is described by a linear fit of a plot of (i) a log of said reduced modulus versus (ii) a log of said ratio of probe penetration depth to the thickness of said layer when a regression coefficient of said linear fit is greater or equal to 0.96.

3. The method of claim 2, wherein said relationship is described by a plot of (i) said reduced modulus versus (ii)

said ratio of probe penetration depth to the thickness of said layer when said regression coefficient is less than 0.96.

4. The method of claim 1, including:
after applying said initial force but before increasing the force on said probe from said initial force to said maximum force, lifting said probe away from said surface to locate the point of zero load and zero displacement.

5. The method of claim 1, including:
between said increasing said force from said initial force to said maximum force and said decreasing said force from said maximum force to said initial force, holding said maximum force for a fixed period of time sufficient to allow for an increase in penetration depth at said maximum force before generating said unload curve.

6. The method of claim 1, wherein said layer of sample material comprises a porous material having a dielectric constant of less than 4.

7. The method of claim 1, wherein said maximum force is equal to less than 50 micro newtons.

8. The method of claim 1, wherein said maximum force is equal to less than 25 micro newtons.

9. The method of claim 1, wherein said maximum force is equal to less than 10 micro newtons.

10. The method of claim 1, wherein said probe penetrates into said layer between 0.1% and 60% of the thickness of said layer at said maximum force.

11. The method of claim 1, wherein said probe penetrates into said layer of said sample material greater than or equal to 10 nanometers.

12. The method of claim 1, wherein said probe has a tip comprising a cube corner and said cube corner has a radius of 40 nm or less.

13. The method of claim 1, wherein said layer of sample material is dry and said indentation is performed in a dry inert atmosphere.

14. A method, comprising:
placing a probe, of a nano-indenter, in contact with a surface of a porous material on a substrate located in an inert atmosphere;
determining an area function of a tip of said probe on a layer of a standard material on said substrate;
measuring a porous material placed in said nano-indenter for measurement;
selecting an initial load, associated with an initial force, configured to balance requirements of a minimum surface perturbation with loads for stabilizing contact of the tip with respect to said porous material;
applying said initial load to said porous material;
measuring, based on said applying, a first displacement value;
selecting a maximum load associated with said initial load;
determining a location of the surface by applying a force of less than 800 nano newtons to the surface;
determining unload characteristics of the porous material using probe pressures selected such that (i) the unload characteristics of the porous material are unaffected by the presence of the substrate and (ii) the probe simultaneously induces elastic and plastic deformation of the porous material; and
performing data analysis of the unload characteristics to determine the relationship between (i) a modulus of the porous material and (ii) a ratio of contact depth to a thickness of the porous material;
using said area function and said unload characteristics to extract said modulus; and
using said modulus, a Poisson's ratio of said porous material, a modulus of said standard material, and a Poisson's ratio of said standard material to determine a Young's modulus of said porous material.

15. The method of claim 14, wherein the relationship is non-linear, and a log-log plot is employed to extract the modulus.

16. The method of claim 15, wherein the relationship is linear, and a linear-linear plot is employed to extract the modulus.

17. A computer program product for determining Young' modulus, the computer program product comprising a computer readable storage medium having program instructions embodied therewith, the program instructions executable by a computer, to cause the computer to:
instruct a nano-indentation device to place a probe, of a nano-indenter, in contact with a surface of a layer of a sample material on a substrate with an initial force of 800 nano newtons or less;
determine an area function of a tip of said probe on a layer of a standard material on said substrate;
measure a low-k sample placed in said nano-indenter for measurement;
select an initial load, associated with said initial force, configured to balance requirements of a minimum surface perturbation with loads for stabilizing contact of the tip with respect to said low-k sample;
apply said initial load to said low-k sample;
measure, based on applying said initial load to said low-k sample, a first displacement value;
select a maximum load associated with said initial load;
determine a location of said surface relative to an initial indentation depth for said initial force;
instruct said nano-indentation device to increase the force on said probe from said initial force to a maximum force, associated with said maximum load, greater than said initial force and to generate a load curve of force versus probe penetration depth;
instruct said nano-indentation device to decrease the force on said probe from said maximum force to said initial force and to generate an unload curve of force versus probe penetration depth, said maximum force selected such that the unload curve is independent of the presence of said substrate;
use said unload curve, determining a relationship between (i) a reduced modulus of said sample material and (ii) a ratio of probe penetration depth and a thickness of said layer;
use said area function and said unload curve to extract said reduced modulus; and
use said reduced modulus, a Poisson's ratio of said sample material, a modulus of said standard material, and a Poisson's ratio of said standard material to determine a Young's modulus of said sample material.

18. The computer program product of claim 17, wherein said relationship is described by a linear fit of a plot of (i) a log of said reduced modulus versus (ii) a log of said ratio of probe penetration depth to a thickness of said layer when a regression coefficient of said linear fit is greater or equal to 0.96.

19. The computer program product of claim 18, wherein said relationship is described by a plot of (i) said reduced modulus versus (ii) said ratio of probe penetration depth to the thickness of said layer when said regression coefficient is less than 0.96.

* * * * *